(12) United States Patent
Hirata et al.

(10) Patent No.: US 8,454,542 B2
(45) Date of Patent: Jun. 4, 2013

(54) POSITIVE PRESSURE CHAMBER FOR EXTREMITIES

(75) Inventors: Hitoshi Hirata, Nagoya (JP); Yoshiki Matsumoto, Komaki (JP); Kenichi Iida, Komaki (JP); Takuya Miyagawa, Komaki (JP)

(73) Assignee: National University Corporation Nagoya University, Aichi (JP)

( * ) Notice: Subject to any disclaimer, the term of this patent is extended or adjusted under 35 U.S.C. 154(b) by 999 days.

(21) Appl. No.: 12/444,801

(22) PCT Filed: Aug. 24, 2007

(86) PCT No.: PCT/JP2007/067078
§ 371 (c)(1),
(2), (4) Date: Jun. 12, 2009

(87) PCT Pub. No.: WO2008/044400
PCT Pub. Date: Apr. 17, 2008

(65) Prior Publication Data
US 2010/0042027 A1 Feb. 18, 2010

(30) Foreign Application Priority Data
Oct. 10, 2006 (JP) .................. 2006-276735

(51) Int. Cl.
*A61H 7/00* (2006.01)
(52) U.S. Cl.
USPC ............................. 601/150; 602/13
(58) Field of Classification Search
USPC ............. 601/17, 46, 55, 61, 148–152; 602/13
See application file for complete search history.

(56) References Cited

U.S. PATENT DOCUMENTS

| | | | | |
|---|---|---|---|---|
| 3,824,992 A | * | 7/1974 | Nicholson et al. | 601/152 |
| 4,206,751 A | * | 6/1980 | Schneider | 601/152 |
| 4,418,690 A | * | 12/1983 | Mummert | 601/152 |
| 5,672,148 A | * | 9/1997 | Maunier | 601/148 |

OTHER PUBLICATIONS

E.Z.Hazarika et al, The Effect of Intermittent Pneumatic Compression on the Hand after Fasciectomy, The Hand, 1979, 309-314, vol. 11 No. 3, UK.

* cited by examiner

*Primary Examiner* — Michael A. Brown
(74) *Attorney, Agent, or Firm* — Konomi Takeshita

(57) ABSTRACT

The present invention provides a positive pressure chamber for treating extremities, which is used for treating extremity swelling or edema, rehabilitation, prophylaxis for deep venous thrombosis, relieving extremity pain, improvement of extremity skin, and the like.

31 Claims, 13 Drawing Sheets

POSITIVE PRESSURE CHAMBER FOR EXTREMITIES

CROSS REFERENCE TO RELATED APPLICATIONS

This application claims priority under 35 U.S.C. 119 based upon Japanese Patent Application Serial No. 2006-276735, filed on Oct. 10, 2006. The entire disclosure of the aforesaid application is incorporated herein by reference.

FIELD OF THE INVENTION

The present invention relates to a positive pressure chamber for extremities for treating and preventing swelling and edema of at least one of the extremities, and a method using it.

BACKGROUND OF THE INVENTION

The extremities, particularly a hand and an arm, are organs composed of bones, muscles, ligaments, tendons, blood vessels, nerves, the skin, and the like and have a very variegated motion and delicate sense, indispensable organs in all human activities from everyday life to creative activity. Furthermore, a hand, which also plays an important role for expression of emotion or an intention, is viewed as a very high sociality organ. Restoration of a hand or reconstruction of a function requires a reconstruction of sophisticated functions and esthetics, prompting the training of specialists (hand surgeons and hand therapists) who specialize in this field in every country in the world.

Further, the hand is an anatomical site to which an externally caused injury occurs most frequently, and as many as 12% of the American emergency patients are hand surgery patient candidates. Further, a hand is a frequent site for work-related musculoskeletal disorders, such as a carpal tunnel syndrome, stenosing tenosynovitis, tennis elbow, and the like, totaling as many as 64% of all work-related musculoskeletal disorders, with the cost of the medical treatment allegedly estimated at 270 billion dollars, and the number of cases is also annually on the rise. However, these diseases occur not just among male workers, but also frequently among middle- and-advanced aged women, mostly housewives. For this reason, it is estimated that female patients are numbered about three times as much as male patients. According to a recent epidemiological research on a most frequent carpal tunnel syndrome, the incidence rate in general population is said to be about 2.7% of the adult population, and the annual number of surgery cases amounts to 200,000 cases in the United States.

Furthermore, for hand surgery, osteoarthritis (estimated to be 70 million patients in the United States) is the 3rd most frequent next to a knee joint and a hip joint, and it is the highest site in the frequency of the inflammatory arthritis exemplified by articular rheumatism.

Although hand surgery demands ample knowledge and experience, and sophisticated medical technique, recovery of the expected function fails to occur unless post operative after-treatment is appropriate, no matter how outstanding the operation was. The most important factors to look for in after-treatment are postoperative edema and pain control. A hand beings a site which is very prone to swell after an externally caused injury or operation, a negligent control, will cause contraction of a ligament or the joint capsule, adhesion of a tendon, nerve strangulation, and the like, lapsing into a serious functional disorder. Further, the incidence of circulatory disorders, unless caught and treated early, will cause a tissue necrosis or muscle's ischemic contracture resulting in a useless hand.

Thus, in the medical treatment after an externally caused injury or an operation of a hand, it is important how one controls a pain and maintains good circulation while controlling edema; further it is also necessary for contracture prophylaxis and recovery of function to start active motion of fingers at an early stage as much as possible.

For this reason, this makes the measures against edema at an early stage after injury or an operation the most important treatment common to all hand surgery operations.

The current therapy for edema control extensively relies on a compressive bulky dressing for an early stage edema control after an injury or operation. The method specifically calls for placing a number of thick gauze layers uniformly around the hand, inserting gauze between the fingers to the extent of not obstructing circulation, and loosely fastening over the layers with an elasticity bandage. Compressive bulky dressing, if executed appropriately, will uniformly press the whole hand and control edema formation. Furthermore, relief of edema is further expedited by keeping the hand from the elbow higher than the heart, thereby easing venous and lymphatic perfusion. In addition, the patient is asked to perform active motion of the fingers within the compressive bulky dressing, so as to further activate venous and lymphatic perfusion. Further, various devices have been reported on encouraging the patient to raise the arm and move the fingers while in use of this dressing method.

It should be noted that the conventional compressive bulky dressing has various shortcomings as shown below.

It does not allow checking how much pressure is being applied or whether the pressure is distributed uniformly or not. It is difficult to long maintain the pressure initially exerted when worn, and the dressing may come to loosen or tighten excessively.

It makes finger motion difficult to do due to interference from the gauze.

It neither allows observing the wounded site nor monitoring inflammation, circulatory disorder, or the like.

It does not allow controlling temperature, preventing cooling or warming as needed.

It makes the arm to be held elevated at all times, which keeps the patient restrained.

Nevertheless, presently with no alternative method as yet developed to replace the compressive bulky dressing, this method, while facing these deficiencies, continues to prevail widely as an established standard medical treatment procedure.

SUMMARY OF THE INVENTION

An object of the present invention, made in light of the above problems, is aimed at providing, in a device and method for treating or preventing the extremities from swelling or pains associated therewith, a device and a method capable of maintaining at all times the extremities under a uniform compressed condition. Another object of the present invention is to provide a device and method which allow free motion of an extremity's distal end, allow simple observation of the wounded site, and allow monitoring inflammation, circulatory disorders, and the like. Further, a still another object of the present invention is to provide a device and method which allows performing an appropriate temperature control, commensurate with the medical treatment procedure of the extremities, in particular cooling and warming as needed. A further object is to provide a device and method which can acquire a necessary drainage effect without requiring the extremities or an arm to be elevated, thereby eliminating the need to restrain the patient.

The positive pressure chamber for the extremities provided by the present invention and treatment method using the same for solving the above problems was developed as a simple environmental control system to manage the condition of a hand in the best after a hand surgery operation, which is also applicable not only to the hand but also the legs.

The fundamental concept is about perfusing air in a disposable type, easy-to-wear chamber for managing the entire hand post-operatively under uniform positive pressure. While the conventional compressive bulky dressing does not warrant that the compression exerted at the time of its application will hold thereafter, which actually continues to greatly change, the inventive positive pressure chamber for extremities is capable of effectively inhibiting post-operative swelling of extremities by having an optimal positive pressure maintained at all times, thereby achieving pain alleviation and contracture prophylaxis.

An extremity's distal end can be moved freely in this positive pressure chamber for extremities, thereby also allowing complete finger motion which has been impossible to do while wearing a compressive bulky dressing. In addition, a peripheral to central fluid flow is applied to, and held on, each of the extremities, which achieves a drainage effect thereon, whereby this also make it unnecessary to keep the affected extremity elevated as done by the conventional device for accelerating venous and lymphatic perfusion. In addition, there is no need as would with the conventional device, for massaging upward in sequence from the peripheral side, or pumping, which involves a repetitive intermittent cycle of compression and decompression.

Furthermore, it is also made possible with this invention to control the temperature and humidity of air or to continuously administer a transdermal medication. While cooling is a very effective means for controlling swelling, there has been no practical procedure to cool the hand through thick gauze in a compressive bulky dressing, so that its implementation has been given up. In contrast, the present invention, for example, enables one to adjust the temperature of the perfusing air, thereby to maintain the inside of the chamber at a uniform temperature, thereby making it possible to flexibly utilize a cooling therapy for swelling and a thermal therapy for circulatory disorders, and the like. Further, the device can be fabricated from a low cost material, is structurally simple, and suitable for mass-production.

Such characteristics as described can qualify the present inventive pressure chamber for extremities and a therapeutic method and a prophylaxis using the same to be a standard post hand-surgery management method to replace the conventional bulky compressive dressing method, with its indication targeted to all patients after hand injuries or surgeries.

While many of the diseases included in work-related upper-extremities musculoskeletal disorders are known to be caused by tenosynovial swelling, the present invention is capable of relieving very efficiently not only hypodermic edema but also the edema developed in deep tissues such as a tenosynovial membrane and a ligament. These characteristics make the present invention applicable not only to postoperative but also conservative treatment of work-related musculoskeletal disorders (including a carpal tunnel syndrome, stenosing tenosynovitis, and the like) which are generally called by the term repetitive strain injury or cumulative trauma injury or the like. Its characteristic of relieving the edema in deep structures, such as a tendon and a ligament, is also a very attractive one in the rehabilitation of a hand, which can be widely applied in this field. Further, for an application to the lower extremities, the devise can be expected to offer a prophylaxis effect for deep venous thrombosis. Since the device is disposable and readily portable, it can be anticipated to find an application other than in medical devices, such as a prophylaxis against the economy class syndrome on a plane, and the like. Thus, a very extensive adaptation is anticipated.

In order to attain the above objects and effects, according to the first main perspective of the present invention, a positive pressure chamber for extremities is provided, which comprises: a bag-shaped member having a bag-shaped main part which is formed to inflate by having a space part sectioned between an exterior sheet member and an interior sheet member filled with fluid, which member is formed in such shape and size that, under a condition in which it is filled with fluid, it can cover the outer periphery of at least one of the extremities; wherein:

said bag-shaped member is formed such that said extremity which is entirely covered with said interior sheet member is held under a positive pressure condition by having the space part of said bag-shaped member filled with fluid and wherein the distal end of said extremity can be moved in the fluid filled in said space part, independently of other parts of the extremity; and wherein said interior sheet member has an inlet for introducing the fluid filled in the bag-shaped member and/or other fluid, from said extremity's distal end side and allows the fluid introduced therefrom to flow along a clearance between the outer periphery of the extremity and said interior sheet member in a direction away from the extremity's distal end.

According to an embodiment of the present invention, said bag-shaped member is formed in size and shape of securing a sufficiently sized space part that the interior sheet member that covers the distal end of the extremity does not interfere with the exterior sheet member when the extremity's distal end is moved in the fluid filled in said space part.

According to another embodiment of the present invention, said interior sheet member further has an extremity's distal end accommodation part, which part is formed to cave in from said interior sheet member into said space part for accommodating at least one distal end of the extremities; and said extremity's distal end accommodation part with the distal end of the extremity inserted therein allows the extremity's distal end to move freely in the fluid filled in said space part. In addition, in this case said extremity's distal end accommodation part is shaped to fit the shape of the extremity's distal end.

According to another further embodiment of the present invention, the inlet formed in said interior sheet member allows said space part to communicate with the extremity's distal end, thereby introducing the fluid in said space part around the extremity's distal end. In this case the inlet formed in said interior sheet member are preferably a large number of fine pores. In addition, the inlet may be a fluid-permeating sheet member provided at a site corresponding to the distal end.

According to another further embodiment of the present invention, the chamber has an outside-fluid inlet path for introducing a fluid other than the fluid in said space part around the extremity's distal end through said inlet of the said interior sheet member.

According to another further embodiment of the present invention, said exterior sheet is provided with a fluid inlet port for introducing said fluid into the space part of said bag-shaped member.

According to another further embodiment of the present invention, said bag-shaped member is configured so as to cover the outer periphery of the extremity with said interior sheet member by folding it with said interior sheet member inside and the exterior sheet member outside; and fasteners are provided at said edges of said exterior sheet member for joining, as folded, together the edges of the exterior sheet member themselves.

According to another further embodiment of the present invention, said interior sheet member is formed of a member which is more flexible than said exterior sheet member and has sufficient anti-burst strength.

According to another further embodiment of the present invention, said exterior sheet member is formed of a transparent member to allow visually checking the movement of the extremity's distal end in the fluid filled therein.

According to another further embodiment of the present invention, the fluid filled in said space part is the atmosphere.

According to another further embodiment of the present invention, said other fluid is a draining fluid. Furthermore, said draining fluid contains a drug to be administered into the body via the skin of said extremity.

According to another further embodiment of the present invention, a positive pressure chamber for extremities is provided which further comprises a flexible tube communicating with the space part of said bag-shaped member; and pump equipment for introducing fluid into said bag-shaped member through said tube; the pressure of the fluid filled in said bag-shaped member by said pump equipment is sufficient to hold said extremity within said fluid and is at a value within the range of equilibrium state with a normal interstitial pressure of said extremity.

In this case, the pressure value of the fluid filled in said bag-shaped member by said pump equipment is preferably not less than 20 mmHg but less than the diastolic blood pressure. Further, the equipment preferably has a means to maintain the pressure of the fluid filled in said bag-shaped member by said pump equipment constant throughout the time that said positive pressure chamber for extremities is operated.

According to another further embodiment of the present invention, it further has a pressure control valve for maintaining the pressure within said space part of said bag-shaped member at a designated value.

According to another further embodiment of the present invention, it further has a member for securing a clearance for the fluid to flow between the skin of said extremity and said interior sheet member. In this case, said clearance securing member is preferably worn beforehand on said extremity before the extremity is applied to said bag-shaped member. In addition, said clearance-securing member may be fixed to a part of said interior sheet member which comes in contact with the outer periphery of said extremity.

According to another further embodiment of the present invention, it further has a fluid recovery means for recovering the fluid which has flowed along the clearance between the outer periphery of the extremity and said interior sheet member in a direction away from the extremity's distal end.

According to another further embodiment of the present invention, it is preferably for controlling edema and pain after extremity surgery, for providing post-surgical management for work-related musculoskeletal disorders; for providing conservative treatment for work-related musculoskeletal disorders; or for use in a transdermal drug delivery.

According to a second main perspective of the present invention, a method is provided for treating, ameliorating, or preventing extremity disorders, comprising a step of supporting said extremity's distal end in a freely movable condition under positive pressure within the range of equilibrium state with a normal interstitial pressure of the extremity; and a step of allowing a draining fluid to flow along said extremity in a direction away from the extremity's distal end, thereby promoting drainage.

According to an embodiment of the present invention, this method comprises applying it to edema and/or pain in an extremity, an extremity's distal end, and/or a deep tissue of the extremity. Further, in an embodiment, the edema and/or pain of said extremity is lymphatic edema, post-surgical swelling, swelling from inflammation or caused by external injuries, swelling by synovitis from rheumatoid arthritis or osteoarthritis, or swelling caused by extravasation from venous catheter, swelling from burns, or swelling from the economy class syndrome. Further, this method is applied after an injury or an operation.

For example, according to such an embodiment, swelling or inflammation of the synovial membrane of a joint can be relieved promptly through the promotion of lymphatic or venous perfusion; this action alleviate the arthritic symptoms seen in the articular rheumatism and osteoarthritis and inhibits a development thereof.

According to an embodiment of the present invention, this method may be applied to work-related musculoskeletal disorders and may be applied to conservative treatment of work-related musculoskeletal disorders. In this case, said work-related musculoskeletal disorder may be carpal tunnel syndrome, stenosing tenosynovitis, or tennis elbow. Further, this method is preferably applied before, during, and or/after work.

According to an embodiment of the present invention, this method is applied to prevention of deep venous thrombosis.

Other features and significant effects of the present invention which have not been set forth above can be comprehended by those skilled in the art by also referring to the drawings attached to the following section, Detailed Description of the Preferred Embodiment.

DETAILED DESCRIPTION OF THE INVENTION

Hereafter, the constitutional elements in an embodiment of the positive pressure chamber for treatment of extremities of the present invention are explained in detail.

Figure 1:
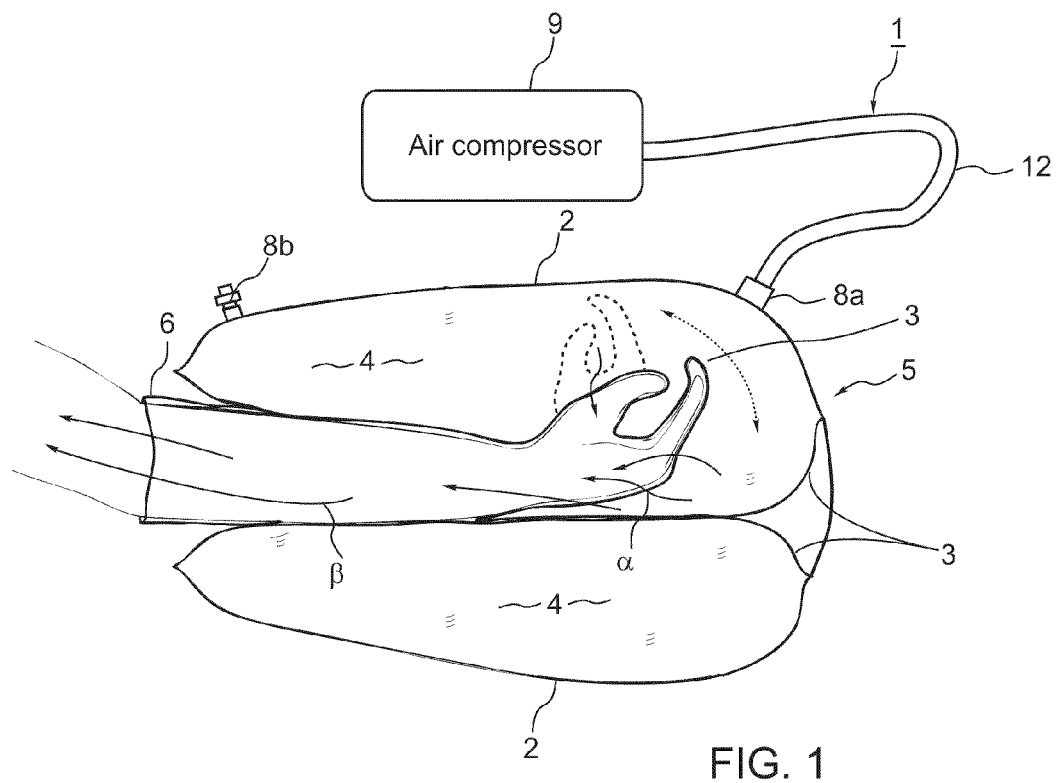
FIG. 1 is a drawing which shows the way a positive pressure chamber for extremities, an example of the present invention, is used.
Figure 2:
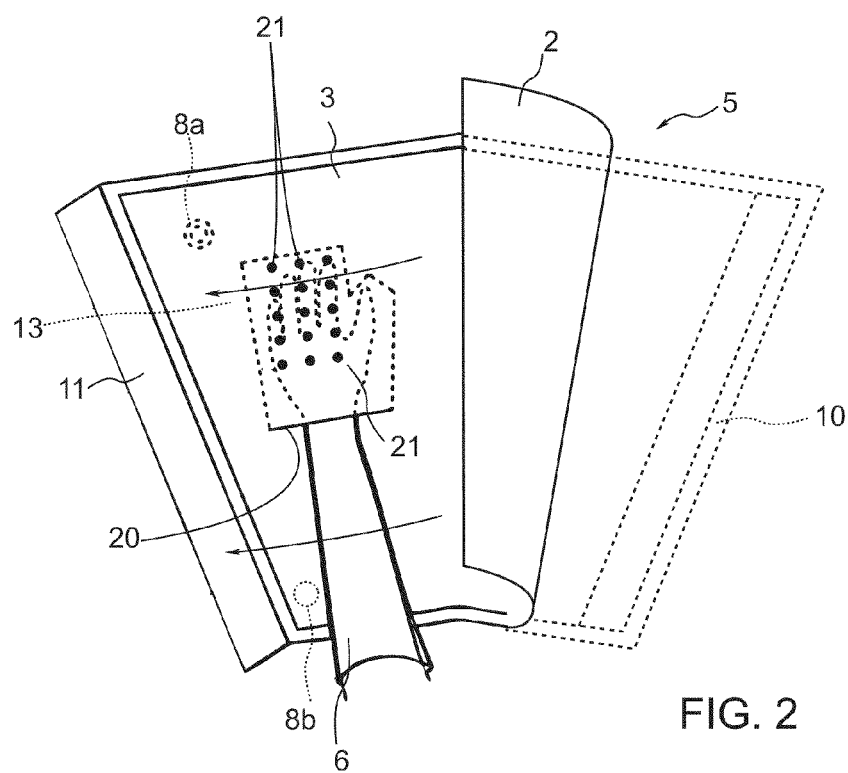
FIG. 2 is a plan view which shows the way said positive pressure chamber for extremities is unfolded.

FIG. 1 is a drawing which illustrates the way a positive pressure chamber for extremities 1 is used in this embodiment. FIG. 2 is a plan view which shows the positive pressure chamber for extremities 1 as it is unfolded.

First, the positive pressure chamber 1 for extremities has a bag-shaped main part 5 (a bag-shaped member of the present invention) which is formed to inflate by having a space part sectioned between an exterior sheet member and an interior sheet member filled with fluid. The interior sheet member 3 of the main part 5 is formed such that, under a condition in which fluid (air in this embodiment) is filled in said space part 4, as in FIG. 1, the outer periphery of the arm and hand can be covered along their contour with the interior sheet member.

Said arm and hand entirely covered with said interior sheet member 3 can be held under positive pressure (not less than 20 mmHg but less than the diastolic blood pressure) within the range of equilibrium state with a normal interstitial pressure of the extremity by having the space part 4 of said bag-shaped member 5 filled with fluid; and the hand (the distal end of the extremity) can be freely moved in the fluid filled in said space part, independently of the arm part.

Further, said interior sheet member 3 has, at a part thereof corresponding to the hand, a large number of pores (not shown in FIG. 1) formed for introducing the fluid filled in the main part 5, so as to let the fluid introduced therefrom permeate through the interior sheet member, as marked with an arrow α, to the surface of the hand flow along the clearance between the outer peripheries of the hand and the arm in a direction from the hand toward the arm (the direction marked by an arrow β).

Further, the hand and arm are equipped with a stocking-shaped clearance-securing member 6 for securing said fluid to flow between the hand and arm and the interior sheet member.

Said exterior sheet member 2 is provided with an inlet port 8a for introducing fluid into said bag-shaped member 5 and inflating said main part 5, thereby maintaining the hand and arm under a positive pressure condition; and the inlet port 8a is placed to allow an air compressor 9 to be connected through a tube. Further, shown in the Figure with 8b is a pressure regulator valve. The regulator valve is set to accurately maintain the inside of said space part 4 under a positive pressure condition of not less than 20 mmHg but less than the diastolic blood pressure.

The wearing of said main part 5 is carried out, as shown in FIG. 2, by folding the main part 5 comprised of an interior sheet member 3 and exterior sheet member 2 joined together so as to enclose the hand and arm therein. When the fasteners 10 and 11 are joined under these conditions and the air compressor 9 is turned on to inflate the main part 5, the part thereof situated underneath the hand and arm functions, as in FIG. 1, like an air pillow, thereby holding the hand and arm at a fixed height.

Such a constitution can provide a pumping effect by virtue of freely moving the hand while having the hand and arm held under positive pressure, and a drainage effect of having the fluid in the main part 5 flowed along the hand and arm skin surfaces. This can activate the hand's and arm's blood and lymphatic flow, thereby effectively reducing or preventing the swelling and edema thereof.

The concept on each constitutional element is now explained in detail below:

(Main Part)

The main part 5 has an air bag structure. By "air bag structure" here is meant a bag-shaped structure formed to enable its inner space to be filled with gas. For example, two identically-shaped sheets, i.e., an interior sheet member 3 and exterior sheet member 2, if overlapped and joined together at their edges, can generate a main part 5 of the present invention. Although the material of the main part 5 is not particularly limited as long as it is a highly airtight material, it is preferred for the material of the main part 5 to be entirely or partially transparent. If the material of the main part 5 is entirely or partially transparent, this will facilitate observing extremity's end part (hand (fingers) in this embodiment), as will be detailed later.

Further, the material of the main part 5 is preferably pliable. The material of the exterior sheet member 2 which will constitute an outer periphery thereof may use one of pliability and some strength, such as polyvinyl chloride and polyethylene terephthalate (PET); and polyurethane film, hydropolymer and the like for their dressing effect. Further, one may adopt a combination of these materials. Still furthermore, with respect to an area which comes in contact with the skin of the extremities, i.e., the interior sheet member 3 does not require strength as much as the exterior sheet member, but needs to be pliable so as to tightly stick along the outer periphery of the extremity, and comes in contact with the extremity via a designated clearance 1; accordingly one may use a hydrocolloid dressing material, which is a substrate material such as polyurethane film coated with a highly water absorbing hydrocolloid; an alginate salt coated material which is coated with a hemostatic alginate salt; and a wound covering material such as a highly hydrated hydrogel-coated hydro-dressing material, hydropolymer, and the like.

Further, as mentioned above, the main part 5 is equipped with a fluid inlet port 8a for injecting fluid into the space part 4 thereof and a pressure regulator valve 8b. In addition, the pressure regulator valve 8b may be mounted on said air compressor or tube 12. In addition, said fluid inlet port 8a and pressure regulator valve 8b are preferably placed in opposite positions. This certainly secures the fluid flow (perfusion) within said main part 5.

Although the method of installing the positive pressure chamber 1 for treatment of extremities of the present invention on an extremity is not particularly limited, it can be installed on the extremity by winding the main part 5 around the extremity or by folding the main part 5 and inserting the extremity therein.

In this case, the positive pressure chamber 1 for extremities is preferred to be nearly fan-shaped in a planar view, as shown in FIG. 2, a shape which expands in progressing from a part corresponding to the extremity base part (arm) to a part corresponding to the extremity's end (hand) of the extremity. It is because if shaped this way, a space can be secured, as will be described later, for freely moving the extremity's end enclosed in the extremity's distal end accommodation part 13. Furthermore, it is because with such a shape, as will be described later, the inflated main part 5 envelops the extremity base (an arm part) for enhanced stability.

An embodiment of the present invention has a fastening means for fastening the main part 5 after having it installed onto the extremity. The fastening means can be made up of a belt, a hook and loop fastener, zipper, or the like; a pair of fasteners 10 and 11 is used in the example of FIG. 2.

(Extremity's Distal End Accommodation Part)

Said interior sheet member 3 is provided with a pocket-shaped extremity's distal end accommodation part 13. Extremity's distal end accommodation part 13 is formed, so as to cave into the space part 4 of the main part 5, for example, from part of the interior sheet member 3, thereby to enclose the extremity's end. The configuration of the extremity's distal end accommodation part is not particularly limited as long as it is capable of enveloping the extremity's end. For example, in this example, as shown in FIG. 2, it can be pocket-shaped which wraps an area from the wrist to the fingertip. When the extremity's distal end accommodation part is made pocket-shaped, it is preferably attached to the main part 5 only via an opening part 20 thereof. This is because this will provide the end of the extremity wrapped in the extremity's distal end accommodation part with improved freedom of movement in the space part 4 of the main part. The extremity's distal end accommodation part 13 is not limited to such shape and may assume any form as long as the extremity's distal end (hand) can be moved independently of the base (arm) under positive pressure.

The material of the extremity's distal end accommodation part 13 may be the same as that of the interior sheet member 3, but one may also use a material more pliable than that of the main part 5. This is so because it will contribute to improved freedom of movement for the extremity's end.

As described above, it is preferred to provide in the space part 4 of the main part 5, under a condition filled with fluid, and between it and the exterior sheet member 2, a space where the extremity's end can be freely moved (see FIG. 1). A space where an extremity can be freely moved means a space such that even when the hand is moved, that movement is not hindered by an interference thereof from the exterior sheet member 2. Such a space can be generated by securing enough sphere of the space part 4 of the main part 5. Specifically, it can be generated by making the distance, in an inflated state, from an opening part 20 of the extremity's end accommodation part 13 to the opposing interior face of the exterior sheet member 2 larger than that from the extremity's distal end to the opening part 20.

In a case where the extremity's distal end accommodation part 13 is provided on the interior sheet member 3, in a construction where the main part 5 is wound around the extremity, the arm portion can be stably immobilized with other parts of the interior sheet member, resulting in a construction where the hand portion alone can be moved with the wrist as an axis. Since this defines the wrist position, accidents can be avoided when the hand is moved within the main part 5, such as damaging the exterior sheet member, the hand colliding with an item outside to hurt the hand, and the like. Further, the entire extremities end up being properly supported by a moderate air-cushioning effect. For example, the distance between the interior face of the interior sheet member 3 constituting the space part 4 and the opposing interior face of the exterior sheet member can be, for example, 10 to 20 cm.

In an embodiment of the present invention, the extremity's distal end accommodation part 13 is provided with a large number of fine pores 21 communicating with the space part 4 of the main part 5. This generate a flow with the fluid in the space part of 4 of the main part 5 permeating through the fine pores 21 to the hand and to the arm, which can activate the venous and lymphatic flow in the vicinity of the skin, a so-called drainage effect, and can at the same time discharge the perspiration generated at the extremity's end or an exudate released from the wounded area. Incidentally, the extremity's distal end accommodation part 13 itself may be made of a porous, liquid-permeable material.

In this embodiment, there is provided a clearance securing member 6 for creating a space for air to flow between the interior sheet member 3 (extremity's distal end accommodation part 13) and the extremity. A drainage effect is acquired only by securing an air flow passage between the interior sheet member 3 and the extremity. The clearance securing member 6 can be formed of an extremity-dismountable elastic fiber member or a net-like structural member. The elastic fiber member that can be used are synthetic fibers such as nylon fibers, polyurethane fibers, and the like, natural fibers, such as cotton, wool, and the like, or a combination thereof. For example, a nylon fiber stocking can be used as a clearance securing member 6.

In addition, the clearance securing member 6 may be constituted by adhering such a material to the interior sheet member 3, in place of a type to be worn on the extremity.

The clearance securing member 6 preferably envelops the entire extremities from an end thereof (hand) to the base (arm); and said clearance securing member 6 preferably extends out from said main part 5. This is because a continuous air passage from the extremity's distal end to the outside is formed whereby the fluid that flowed along the extremity's skin is discharged to the outside, providing a reliable drainage effect.

The positive pressure chamber 1 for the extremities can be used in various applications, and can be used specifically for each application with various attachments.

For example, the positive pressure chamber 1 for the extremities is used for distal extremities with lymphatic edema, post surgical swelling, swelling from inflammation or caused by external injury, swelling by the synovitis from rheumatoid arthritis or osteoarthritis, or swelling caused by extravasation from venous catheter, swelling from burns to relieve said edema or swelling. It is also used to provide post surgical management for work-related musculoskeletal disorders and/or to provide conservative treatment for work-related musculoskeletal disorders.

In the case of extremity's distal end swelling from burns, it is preferred to be equipped with a temperature regulator and a humidity regulator. This is because the temperature regulator and humidity regulator will bring the temperature and moisture of the extremity's distal end to appropriate levels. Further, in an application to the conservative treatment of work-related musculoskeletal disorders, this positive pressure chamber for the extremities is preferably applied before work begins, during or after work.

Further, the positive pressure chamber 1 for extremity treatment of the present invention is used for easing pain accompanied by extremity swelling and/or edema.

Further, other use of the positive pressure chamber 1 for extremity treatment of the present invention includes improvement of the skin quality of an extremity's end. In additional other embodiments, the chamber is used to ease extremity pain.

Further, this positive pressure chamber 1 for extremities can be used for prophylaxis of extremity thrombosis, for example, from the economy class syndrome.

Furthermore, the positive pressure chamber 1 for extremities can be used in a so-called drug delivery. For example, introduction of a drug needed for treatment by convert it to a misted form to the midst of said tube 12, along with the various above-mentioned treatments, may be made to transdermally administer that drug. In this case, the mist form drug which first filled the space part 4 is injected from the fine pores 21 provided in said extremity's distal end accommodation part 13 to the extremity's distal end. As the injected drug thereby flows along the extremity skin, it is transdermally absorbed. This device may be used with a sole objective of transdermally administer a drug unrelated to extremity treatment, not for the objective of treating said extremity swell, edema, and the like.

Further, the above-mentioned embodiment called for the liquid with a drainage effect when introduced over the extremity surface, to be introduced through the fine-pores 21 provided on the extremity's distal end accommodation part 13, without being limited thereto. For example, a tube may be connected directly to an extremity's distal end accommodation part 13 so as to introduce a draining fluid through the tube from outside of the positive pressure chamber for extremities. In this case the draining fluid may be of the same as, or of a different kind from, the fluid which is filled in the space part 4. In addition, when a tube is connected directly to an extremity's distal end accommodation part 13 so as to inject therethrough a draining fluid, it is permissible not to provide the extremity's distal end accommodation part with said fine pores so as not to introduce the fluid in the said space part 4 to the extremity surface.

In this case the draining fluid may be a fluid containing a designated drug. In order to recover said draining fluid or the drug, a tube for recovering said drug may be attached to the extremity base (arm) site, thereby drawing a vacuum to a designated pressure through the tube so as to forcibly recover the draining fluid which flowed over the extremity surface.

The actual application examples for embodiments of the present invention are explained below.

EXAMPLES

Figure 3:
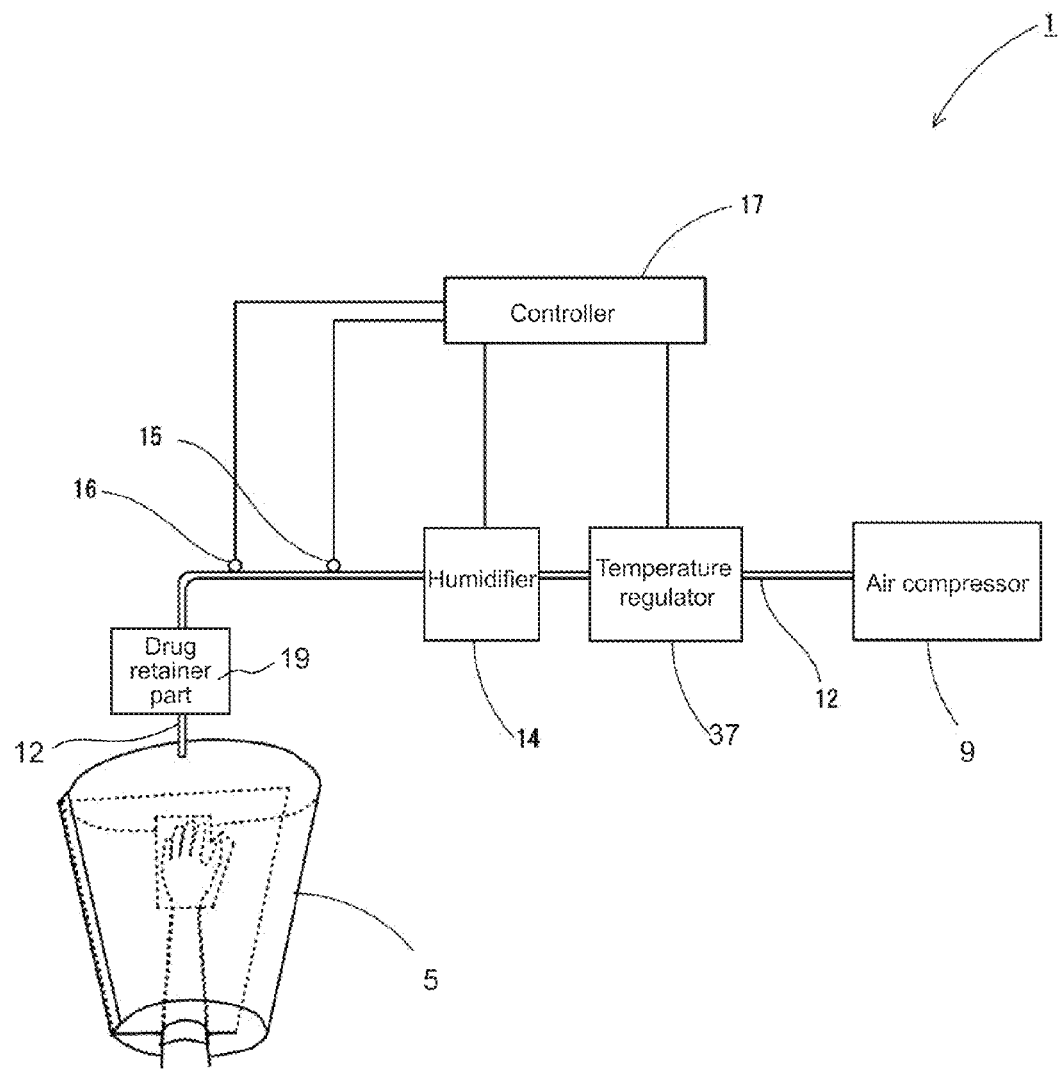
FIG. 3 is a schematic diagram which shows a functional construction of said positive pressure chamber for extremities.

FIG. 3 shows a schematic diagram representing the constitution of a positive pressure device for extremity treatment, which is an example of the present invention. This positive pressure device for extremity treatment is comprised of a positive pressure chamber 1 for extremity treatment, an air compressor 9, a tube 12, a temperature regulator 37, a humidifier 14, a temperature sensor 15, a humidity sensor 16, and a controller 17.

First, the outline of the present device 1 is explained. The air compressor 9 is connected so that compressed air can be fed into the main part 5 through the tube 12.

The temperature regulator 37 is connected to the tube 12, and the compressed air which passes through the tube 12 can be cooled. Further, the humidifier 14 is connected to the tube 12 and the compressed air which passes through the tube 12 can be humidified. Furthermore, the temperature sensor 15 and the humidity sensor 16 are connected to the tube 12. Both sensors 15 and 16 detect the temperature and humidity of the compressed air which flows in the tube 12. Both sensors 15 and 16 transmit the detected data to the controller 17. The controller 17 controls the temperature regulator 37 and humidifier 14. In addition, the temperature regulator 37 and humidifier 14 can also be mounted on the air intake side of the air compressor 9.

Further, between the humidifier 14 and the positive pressure chamber 1 for extremities is installed a drug retainer 19 for retaining a drug for a transdermal administration and misting the drug to be blended in with the compressed air.

Figure 4:
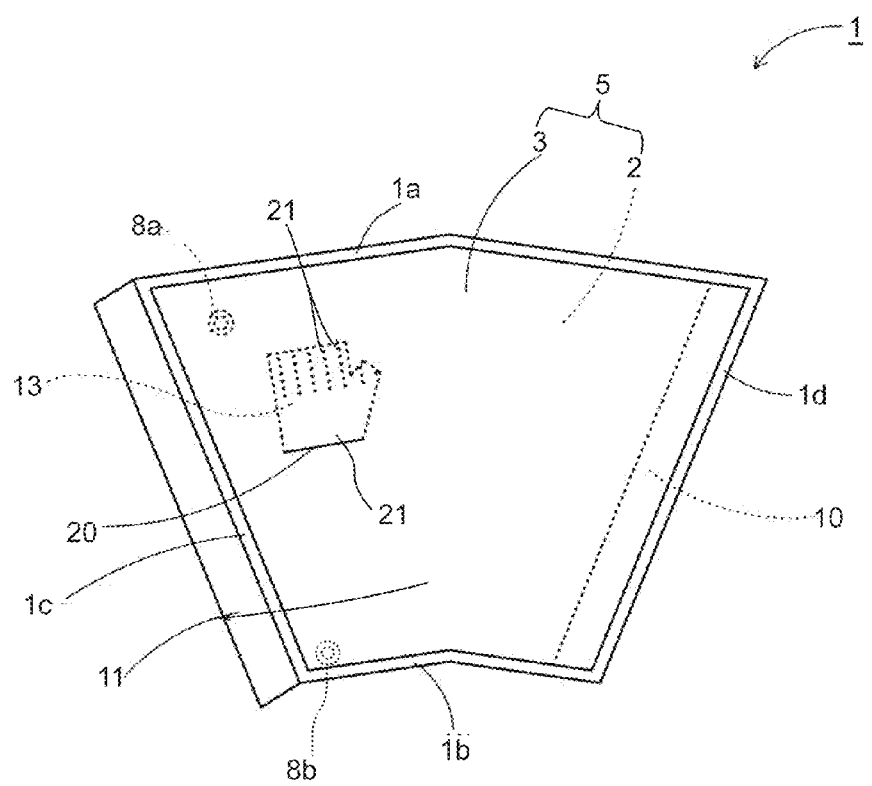
FIG. 4 is a plan view of said positive pressure chamber for extremities in a pre-use condition.

FIG. 4 is a plan view of the positive pressure chamber 1 for extremities.

In this embodiment, the interior sheet member 3 is made of translucent poly vinyl chloride and the exterior sheet member 2 is made of colorless and transparent poly vinyl chloride. The interior sheet member 3 and exterior sheet member 2 are both nearly fan-shaped and have an upper edge part 1a corresponding to a long arc part thereof and a lower edge part 1b corresponding to a short arc part, together with an edge part 1c and an edge part 1d. The interior sheet member 3 and the exterior sheet member 2 are bonded together with heat and pressure at respective edges 1a to 1d. This results in forming an airtight bag-shaped space part 4 on the main part 5 (See FIG. 1).

The interior sheet member is provided with a pocked-shaped extremity's distal end accommodation part 13 practically at a center thereof near the edge part 1c. The extremity's distal end accommodation part has an opening part 20. The extremity's distal end accommodation part 13 is connected to the interior sheet member 3 so as to cave in the space part 4 at the edge of opening part 20. The extremity's distal end accommodation part 13 is sufficiently larger than the size of the hand and is shaped, in a planar view, to comply with the contour of the hand being made up of two sections for the thumb and the remaining 4 fingers. The extremity's distal end accommodation part 13 is provided, at a distal end thereof, with a large number of fine pores communicating with the space part 4 at a designated spacing. On the other hand, the exterior sheet member 2 is provided with air inlet port 8a. The air inlet port 8a is designed to be connected to the tube 12 so that compressed air can be injected to said space part 4.

Further, the exterior sheet member 2 is provided at the edge 1d side one set of the hook and loop fasteners 10 while at the edge part 1c side is provided the other set of hook and loop fasteners 11 which is mounted extended from the interior sheet member 3. The main part 5 is so set up that it can cover the hand and arm by folding it thereby to join the both sets of hook and loop fasteners 10 and 11.

Figure 5:
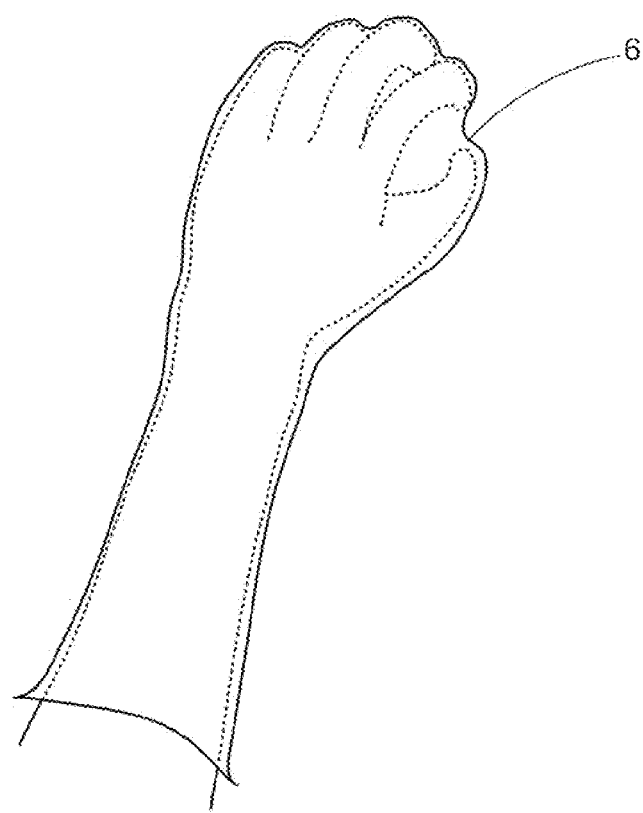
FIG. 5 is a perspective view of a clearance-securing material used in said positive pressure chamber for extremities.

Further, the clearance securing member 6 which is worn on the arm and hand is as shown in FIG. 5 and is formed of nylon fiber fabric such as a stocking; it is worn beforehand on the hand and arm, in order to secure the clearance for an air flow between the arm and hand, and the interior sheet member 3.

Figure 6A:
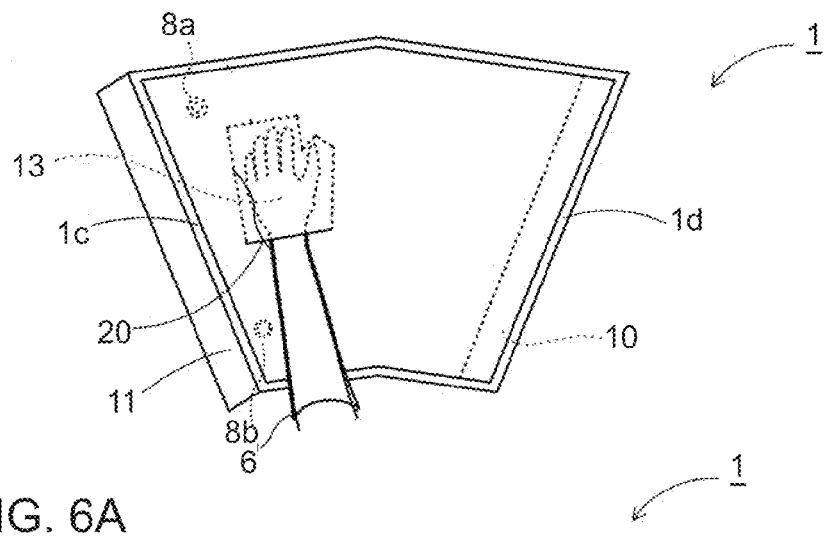
FIGS. 6A, 6B, and 6C are schematic diagrams which show the steps of wearing said positive pressure chamber for extremities.
Figure 6B:
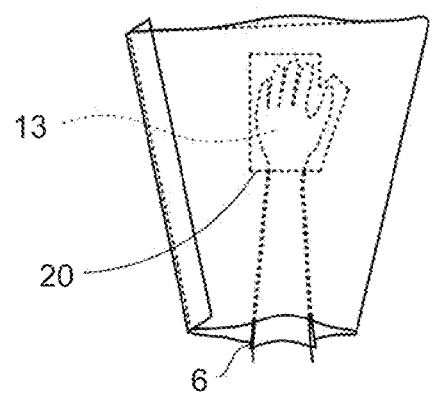
Figure 6C:
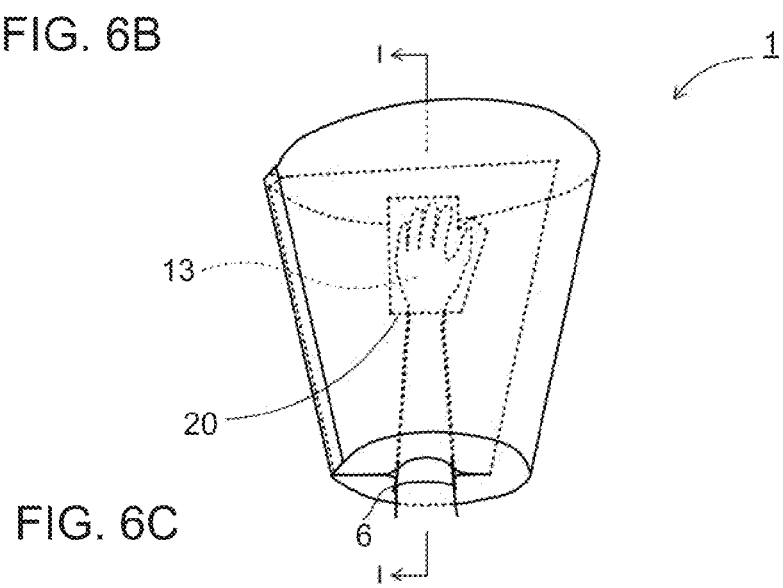

FIGS. 6A to 6C give schematic drawings illustrating a method by which the positive pressure chamber 1 for extremities is mounted on the arm; FIGS. 7A to 7G depict the actual manner thereof.

First, as shown in FIG. 6A (FIG. 7A), insert a hand into the extremity's distal end accommodation part 13 from the opening part 20. Then, fold the main part 5 from the edge 1d side to the edge 1c side to envelop the arm; and join the hook and loop fasteners 10 and 11 (See FIG. 6B and FIG. 7). Then, inject air by the air compressor 9 from the air inlet port 8a into the space part 4. This fills the space part 4 with air, bringing the main part 5 to an inflated state (See FIG. 6C, FIGS. 7C, and 7D). Once filled with air, the air in the space part permeates through the fine pores formed in the extremity's distal end accommodation part 13 toward the hand and escapes toward the arm for drainage, but the internal pressure is maintained at a designated positive pressure (not less than 20 mmHg but less than the diastolic blood pressure). The air compressor flow rate is set at a level appropriate for maintaining said pressure in said space part 4, in accordance with the amount of the fluid used for drainage; for example, it is set at about 3 L per minute in this embodiment. Further, as explained above, installation of a pressure regulator valve 8*b* for a more accurate control of the pressure in the space part 4 will much simplify the control.

Figure 8A:
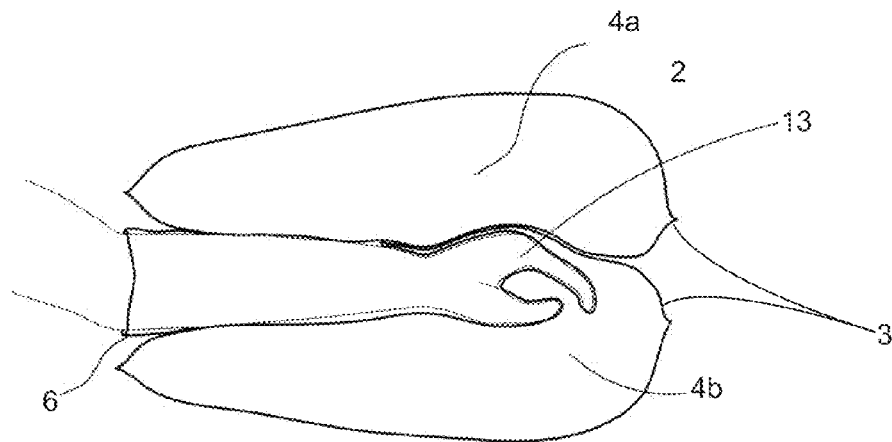
FIGS. 8 A-C are I-I line longitudinal cross sections of FIG. 6C.

The longitudinal cross sections taken on Line I-I in FIG. 6C are shown in FIGS. 8A, B and C. As shown in FIG. 8A, folding the main part 5 divides the space part 4 into a space part 4*a* on the back of the hand side and a space part 4*b* on the palm of the hand side. Since the draining fluid flows along the arm's surface to be discharged to the outside, said interior sheet member is in a state of being stuck fast to the arm's surface, thereby immobilizing the entire arm in situ within the main part 5.

The hand enveloped in the extremity's distal end accommodation part 13 is in a state of being stuck fast to the interior sheet member 3 for the same reason as above, but the hand can be moved freely under positive pressure because the extremity's distal end accommodation part 13 itself is not immobilized.

Figure 8B:
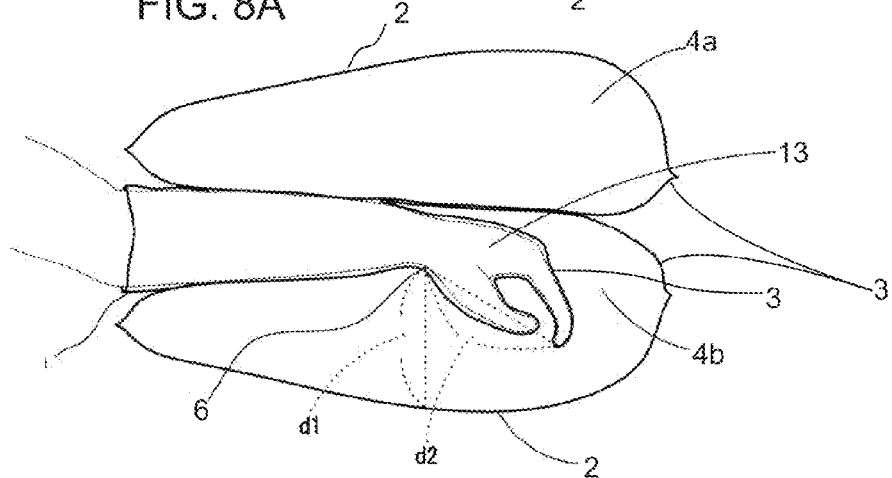

As shown in FIG. 8B, in an inflated state, the distance d1 from the opening part 20 to the opposing exterior sheet member 2 is greater than the length of the hand d2 (the distance from the middle finger tip to the wrist). The space part 4*b* is filled with air, exerting no hindrance to the movement of the hand. Thus the hand and the fingers thereof can be freely moved (See FIGS. 7E and 7F).

Figure 7A:
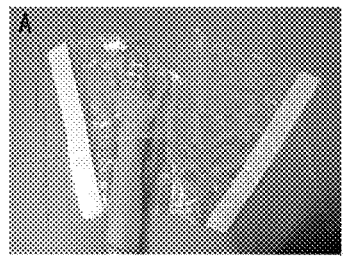
FIGS. 7 A-G are figures which show the steps of wearing said positive pressure chamber for extremities.
Figure 7B:
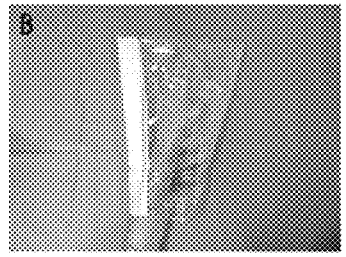
Figure 7C:
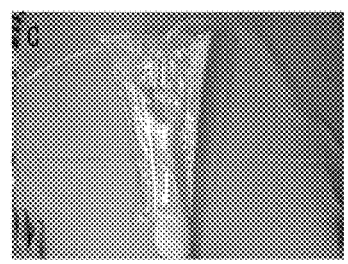
Figure 7D:
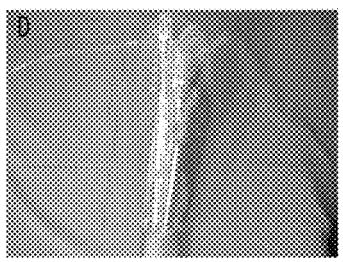
Figure 7E:
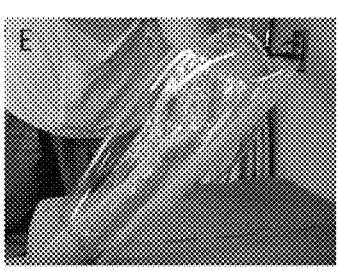
Figure 7F:
Figure 7G:
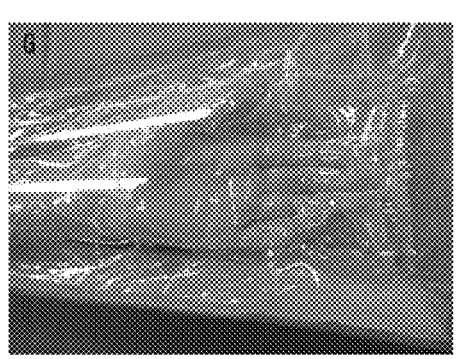
Figure 8C:
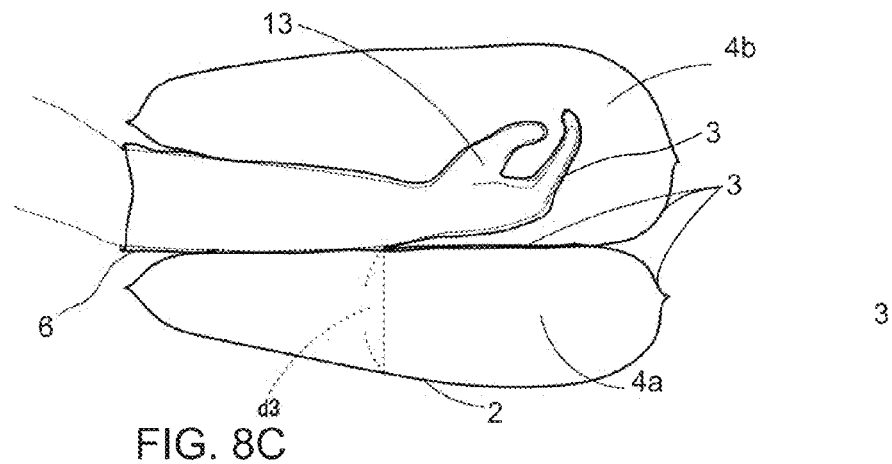

Further, as shown in FIGS. 8C and 7G, rotating the chamber 1 as a whole to bring the back of the hand to be on the downside, this will orient the arm to rest via the interior sheet member 3 on the space part 4*b*.

Such a positive pressure chamber 1 for extremities provides the following advantages:

Operating the chamber 1 will place the extremities as a whole including the hand and arm under uniform positive pressure. The pressure, at a level of about 1 m depth of water, is in equilibrium state with a normal extremity interstitial pressure so that neither the hand nor arm will produce venous congestion.

In addition, as the hand can be moved freely under said positive pressure; the pumping effect can activate the movement of the peripheral blood stream and lymph. Further, the arm's skin receives a vibration by allowing the air in the space part to permeate from the hand tip and flow along the hand skin toward the arm (from peripheral to central nerve), thereby activating the movement of the peripheral blood stream and lymph in the vicinity of the hand skin; this together with the above pumping effect by the hand, can provide an effective drainage effect.

This makes it possible to effectively prevent swelling and edema.

It should be noted that the moving of the hand in compression using the conventional gauze and an elasticity bandage ran a risk of changing the compressed state and lowering the preventive effect on swelling or edema. Further, when compressed too tightly, there was a risk of venous congestion and the like. On the other hand, in the present device, even if a tip of the extremity (hand) is freely moved, the fact that it is under positive pressure remains unchanged, resulting in no reduction in the preventive effect on swelling or edema. This means that the patient is freed from the pain associated with his hand being immobilized.

Furthermore, as shown in FIG. 8C (FIG. 7G), with the palm held upward, the arm will be located between the upper space part 4*b* and lower space part 4*a*. In this case, the lower space part 4*a* will provide an air cushioning effect thereby to support the arm in a stabilized condition by a moderate repulsive force. As a result, even when the patient is in a state of lying on the bed, the arm assumes a stabilized state, thereby lightening the burden on the patient wearing the chamber 1. Further, the chamber 1 is roughly fan-shaped, a shape expanding in progression from the arm's base (lower edge part 1*b*) toward the hand. This ends up generating a broad space part 4 in the vicinity of the hand, thereby securing a region where the fingers of the hand and hand joints are freely moved. Further, the space 4 at the arm's base is smaller than at the vicinity of the hand, whereby the base part is stably gripped.

The extremity's distal end accommodation part 13 of the chamber 1 is sufficiently larger than the size of a hand. Therefore, when the device is worn, there is very little physical interference to the hand when the hand is inserted into a extremity's distal end accommodation part 13. This permits applying the device even to a post surgical wounded site, which is extremely sensitive to physical interference. In addition, since after the main part 5 is folded in two followed by enveloping the arm, it is brought to an inflated state before it is worn so that there is also little physical interference to the base part of the arm and it can be suitably used for an arm with a postsurgical wounded site.

Further, the main part 5 is constituted of a transparent or translucent interior sheet member 3 and exterior sheet member 2. Thus, the hand and the arm can be easily observed even when the chamber 1 is worn. In addition, as mentioned above, the hand can be freely moved, thereby further facilitating observation in a state with the chamber worn on.

Further, said device can also provide additional functions in accordance with the disorder and post operative condition.

That is, the chamber 1 is equipped with a temperature regulator 37. The temperature regulator 37 can cool the compressed air released from the air compressor 11. This contributes to prevention of edema at a wounded site of the postoperative hand. The chamber 1 is also equipped with a humidifier 14. The humidifier 14 can raise the humidity of the compressed air released from the air compressor 9. This can prevent the wounded site from excessively drying, which might be threatened by the air stream which flows from the space part 4 through the clearance securing member 6 to the vicinity of the base of the arm. In addition, the operating conditions of the temperature regulator 37 and humidifier 14 are controlled by the controller 17. The controller 17 is programmed to turn on/off the temperature regulator 37 and humidifier 14 based on the data detected by the temperature sensor 15 and the humidity sensor 16. The program can be arbitrarily set in accordance with the conditions (occurrence and progress of swelling and/or edema, and level of healing of the wounded site) of the extremities which use the chamber 1, the ambient air temperature and humidity.

The device is equipped with a drug retainer part 19. The retainer is set up so that retaining a drug in the drug retainer part 19 makes it possible for the drug retainer part 19 to mist the drug to be blended in with the air which is introduced to the main part 5. As described above, the drug blended in with the air stream is designed to flows in a direction from the hand tip to the arm, and to be transdermally absorbed.

Although chamber 1 was pressurized continuously by the air compressor 9 even after it reached an inflated state, it can be pressurized periodically. Periodic pressurization will provide the hand with pulsation. Pulsation, if applied, can enhance the draining effect. In addition, this will expedite the arm's venous and lymphatic flow. Pulsation may be generated not by installing any special equipment but by the vibration generated by said air compressor; or else ultrasonic vibration may be applied by bursting fine bubbles.

Although the main part 5 was worn on the arm in the present device 1, the site to be worn is not limited to an arm, and may be applied to any one of the extremities. If worn on the leg in particular, this will expedite the venous and lymphatic flow, thereby offering preventive effect on deep venous thrombosis. There is a risk of the incidence of deep venous thrombosis in a situation where the legs cannot be freely moved in confined spaces, for example, as in long-distance air or train travel. The present device, highly portable and transportable, can be suitably used even in such confined spaces.

In this embodiment, the present chamber 1 is equipped with one main part without being limited thereto. For example, it may have multiple main parts each of which is a pressurizable positive pressure device for extremity treatment. If constructed in this manner, the present device can be used simultaneously for multiple extremities. It is also possible to make the main part 5 disposable (throwaway). Constructed in this manner, that will not only enhance the device in hygiene, but will also offer advantages in the production cost of the present device.

Further, the present chamber 1 in this embodiment was used for the arm with a postoperative wounded site, without being limited thereto, but it be used for rehabilitation of extremities days after operation and also for prevention of swelling or edema of unaffected extremities.

Further, the present invention is not limited to the above one embodiment, and can be modified in various ways within the scope of not changing the gist of the present invention.

Figure 10A:
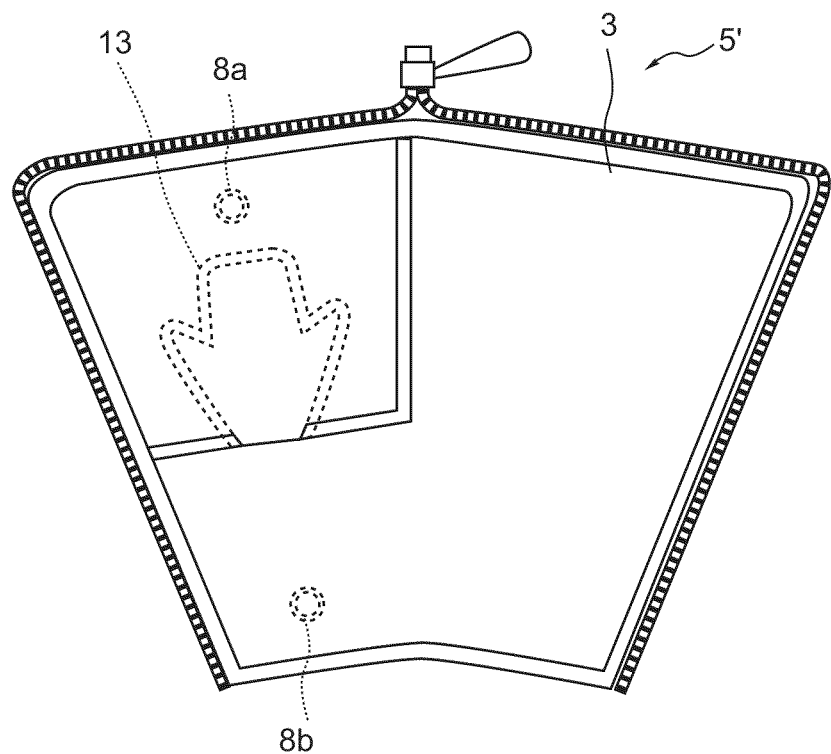
FIGS. 10A and 10B are plan views of the pre-use conditions of a variant example of said positive pressure chamber for extremities.
Figure 10B:
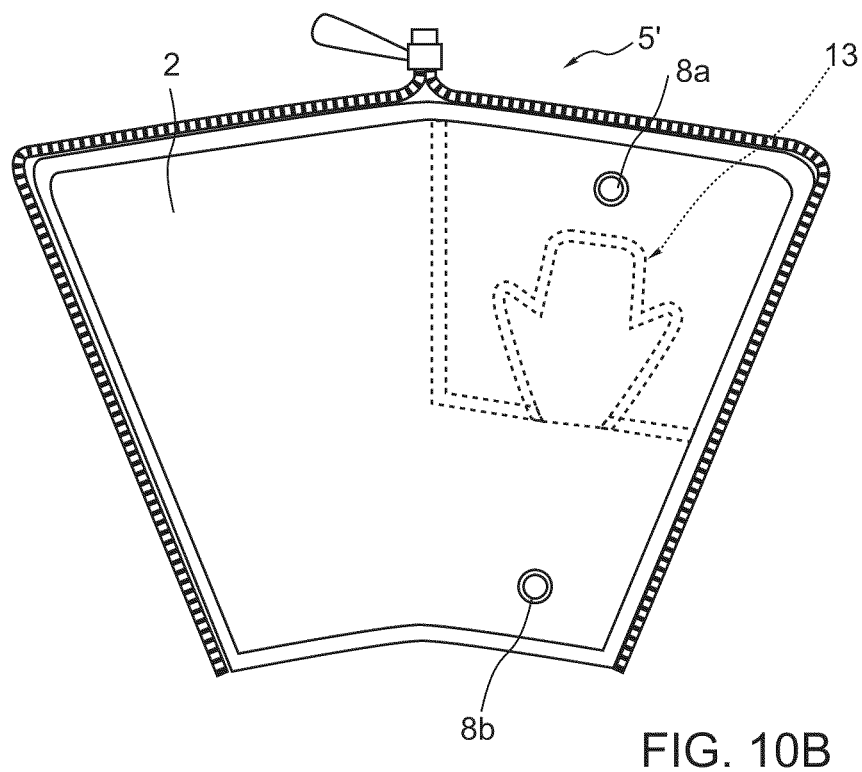

For example, the above one embodiment used a hook and loop fastener, although not limited thereto, to wear the main part on, and fix it to, the arm and hand. For example, as illustrated in FIGS. 10A and 10B, a zipper may be used to close all three sides. This construction can be expected to completely prevent the interior sheet member 3 from being exposed to the outside for protection of the interior sheet member 3, and at the same time to increase pressure retention efficiency within the space part 4.

Further, FIG. 10A is a view of the positive pressure chamber for extremities 1 of this embodiment as seen from a interior sheet member 3 side; and FIG. 10B is one seen from the exterior sheet member 2 side. In this example, the extremity's distal end accommodation part 13 is formed by folding part of said interior sheet member 3 and crafting the folded part into the shape of a hand, thereby generating a pocket-shaped extremity's distal end accommodation part 13. In addition, in this example, in order to be accessible to both the left and right arms, said extremity's distal end accommodation part 13 has sections therein to accept the thumbs on both left and right sides.

Figure 11:
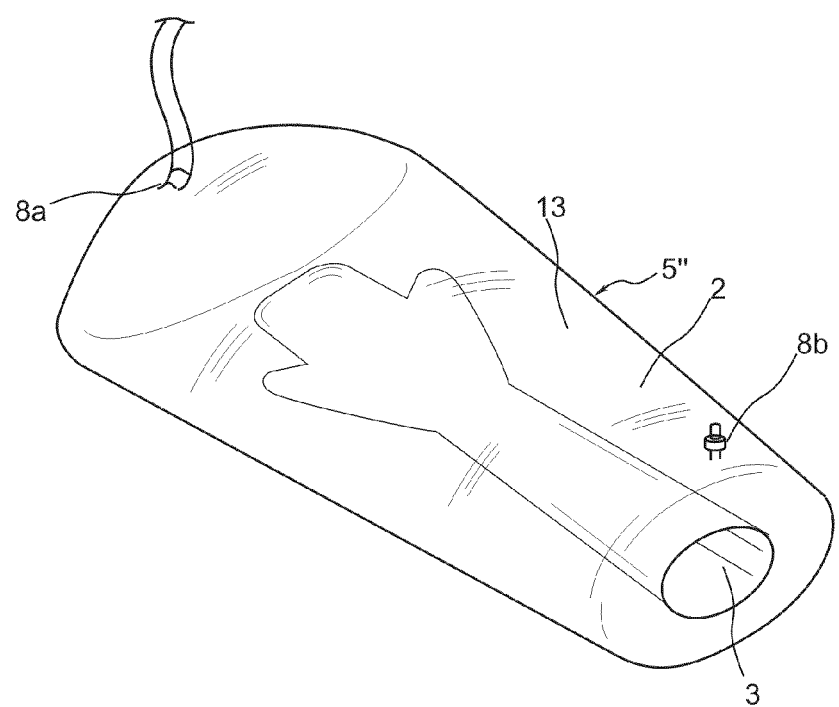
FIG. 11 is a perspective view of the pre-use conditions of a variant example of said positive pressure chamber for extremities.

Further, a positive pressure chamber for extremities 5" which is shaped as shown in FIG. 11 is also acceptable. Although the above-mentioned examples all called for wearing the chamber by winding a sheet member around the arm, it may be constructed such that inflating the space part 4 by introducing fluid therein to be inflated into the shape depicted in FIG. 11.

Figure 12:
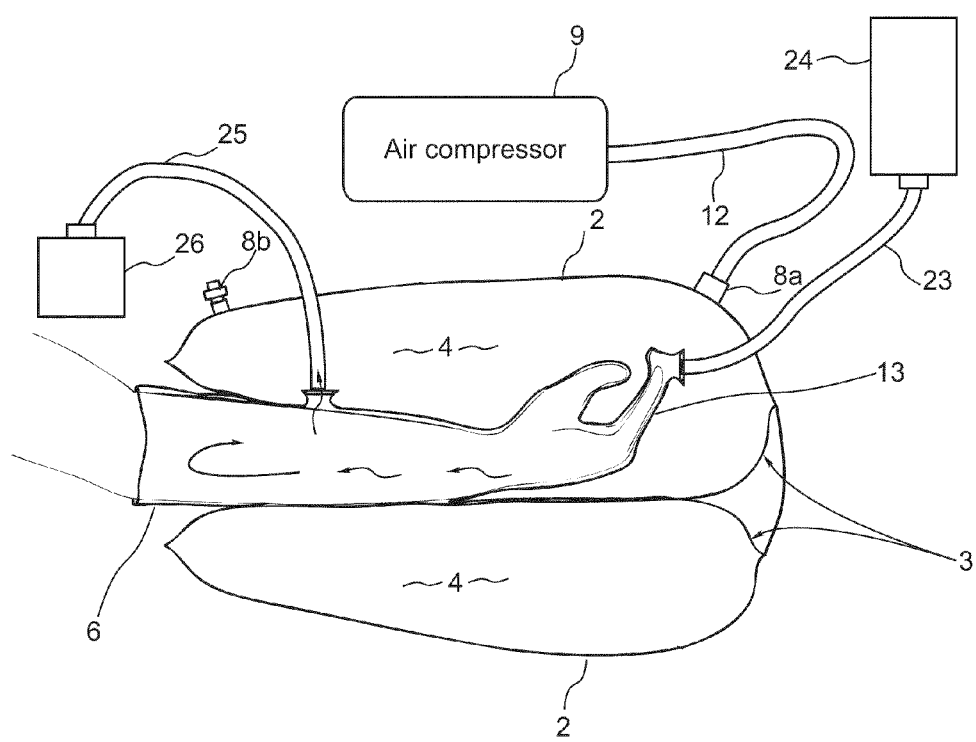
FIG. 12 is a drawing which shows in-use conditions of a variant example of said positive pressure chamber for extremities.

For use of such positive pressure chamber for extremities, the hand and arm can be placed under positive pressure and enables the hand portion to be freely moved by introducing fluid into the chamber 1 while a hand and arm is inserted therein can place Furthermore, shown in FIG. 12 is an example which can perform a transdermal drug delivery to extremities. In this example, a drug delivery tube 23 is directly connected to the extremity's distal end accommodation part 13, in which the drug is injected, through the tube 23, from a drug feeder part 24 installed outside of the positive pressure chamber for extremities. In this case, the drug also serving as a draining fluid makes it unnecessary to provide the afore-mentioned fine pores 21.

Further, this example has a drug recovery tube 25 installed at a part corresponding to the arm of said interior sheet member 3 for recovering an excess drug which was not transdermally absorbed. Aspiration through the tube 25 by an aspirator 26 between the extremity and the interior sheet member 3 at a designated flow rate or pressure makes the drug flow along the skin and at the same prevents the drug from splashing into the air.

Figure 13:
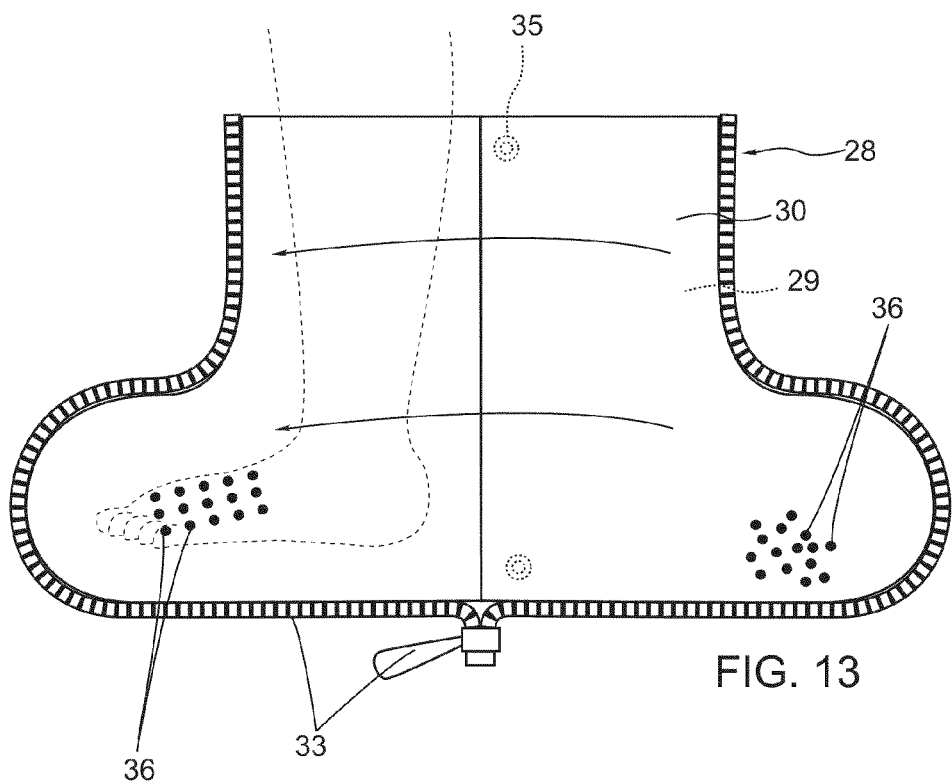
FIG. 13 is a plan view which shows unfolded conditions of a positive pressure chamber for extremities of another example of the present invention.
Figure 14:
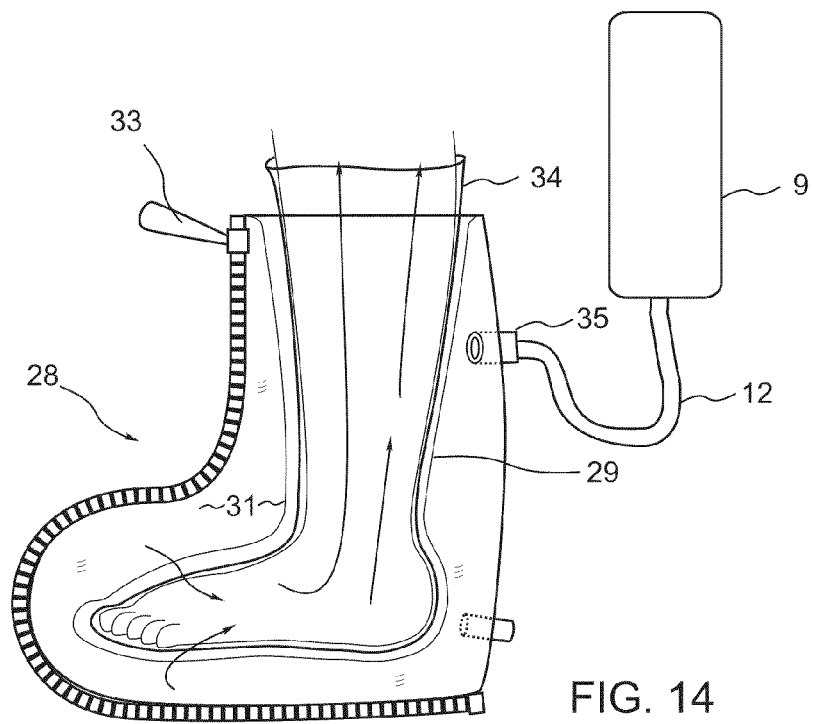
FIG. 14 is a drawing which shows in-use conditions of a positive pressure chamber for extremities of another example of the present invention.

FIGS. 13 and 14 show examples of a positive pressure chamber for extremities 28 applicable to an extremity foot. FIG. 13 is a plan view showing the way in which the chamber is unfolded before being worn; FIG. 14 is a longitudinal cross section showing the way in which it is worn.

This example also has a bag-shaped main part 32 which calls for joining an interior sheet member 29 and an exterior sheet member 30 thereby generating a space 31 therebetween. The chamber is formed bilaterally symmetrically, is folded with the foot placed in the center thereof, and joined along the edges thereof with a zipper 33 to be worn on the foot. In this case a stocking-shaped clearance securing member 34 is worn on the foot.

Then air is introduced through an air inlet port 35 into the space part 31 to inflate the chamber. Said interior sheet member 29 is made of, for example, a piece of thin [poly]vinyl chloride sheet and is equipped with a large number of fine pores 36 for introducing fluid in the space part at a position corresponding to the foot tip part to the foot tip. This causes the draining fluid to flow from the foot tip toward the leg while stimulating the surface of the skin along the clearance secured by said clearance securing member, and finally to be discharged to the outside.

Further, with the draining fluid flowing in this manner, the interior sheet member 29, as shown in FIG. 14, sticks to the surfaces of the foot and leg thereby retaining them in situ. Further, the foot and fingers are held under a designated positive pressure in a space part which is secured within the space part 31 between the interior sheet member and the exterior sheet member, and they can be moved. Since the foot is less mobile than the hand and can have sufficient mobility secured even in a pinched configuration, it needs less space than does the hand.

The fluid in the space part 31 in this embodiment is introduced by an air compressor where its flow rate is determined by the rate at which it is held at positive pressure (not less than 20 mmHg but less than the diastolic blood pressure) under a condition where said drainage is in progress.

Such a construction can provide a positive pressure chamber for extremities also applicable to the foot and leg.

Although an extremity's distal end accommodation part is not installed in this example of the foot, it is permissible, as with the examples for the hand, to provide the interior sheet member 29 with a pocket-shaped extremity's distal end accommodation part for inserting the foot. Conversely it is not always necessary to have an extremity's distal end accommodation part in the examples of the hand as long as the movement of the hand can be secured.

Next, clinical examples of the present invention are explained.

Clinical Example 1

After a patient with the whole hand swollen from stenosing tenosynovitis and having a hardened finger joint has satisfactorily undergone an informed consent by the surgeon, the present device 1 was applied to said affected site (finger) as the first example thereof.

In this clinical example, this device was applied as equipped with an air compressor directly attached to the main part, but without any heater, humidifier, or drug retainer part.

Figure 9C:
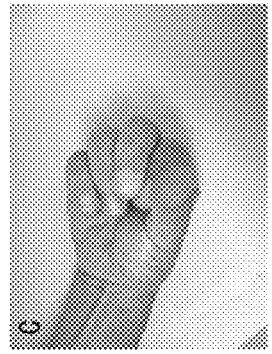
FIGS. 9 A-C show the conditions of the patient's fingers prior to application of the positive pressure chamber for extremities.
FIGS. 9D and 9E show the conditions of the fingers in the patient wearing said positive pressure chamber for extremities.
FIGS. 9F and 9G show the conditions of the fingers in the patient after application of the positive pressure chamber for extremities.
Figure 9B:
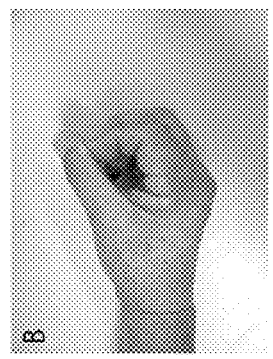
Figure 9E:
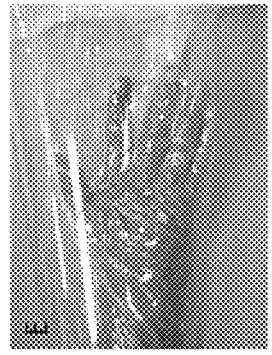
Figure 9G:
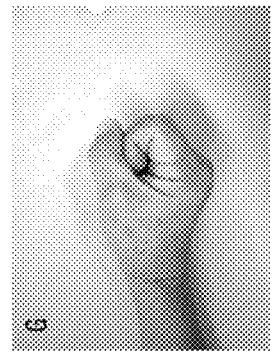
Figure 9A:
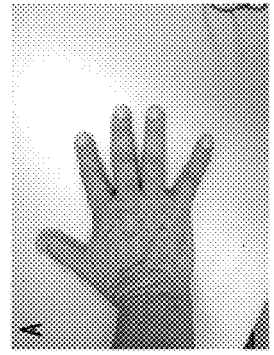
Figure 9D:
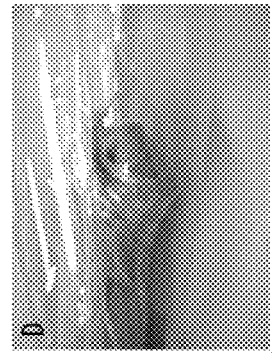
Figure 9F:
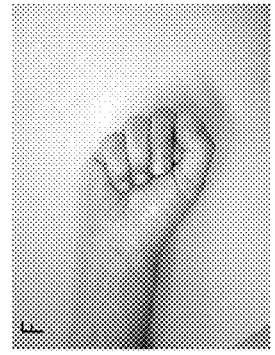

The conditions of the affected area before this device 1 was applied are shown in FIGS. 9A to 9C. The conditions of the fingers after the present device 1 was worn are shown in FIGS. 9D and 9E. The conditions of the fingers after the present device 1 was applied are shown in FIGS. 9F and 9H. As shown in FIG. 9A, the patient's fingers are diffusely swollen. Furthermore, as shown in FIGS. 9B and 9C, the patient's fingers are such that their bending is limited due to the hypertrophy of the peritenon, a tendency most pronounced with the middle finger. The ranges of motion of the patient's fingers, both for active and passive ranges thereof, are limited on the whole, most notably with the middle finger. To such fingers applied the present device 1.

As demonstrated in FIGS. 9D and 9E, the patient's entire fingers can be freely moved under a condition in which they are uniformly compressed in a pressurized chamber 1. When the fingers were repeatedly bent and stretched in the chamber 1, it was confirmed that the fingers' active range of motion has expanded. The fingers were repeatedly bent and stretched in the chamber 1 for another 20 minutes. As shown in FIGS. 9F and 9G, immediately after the fingers were repeatedly bent and stretched in the chamber 1 for a total of 30 minutes, the fingers were freed from swelling thereby enabling the fingers to be completely bent. This indicates that the device 1, if applied to fingers afflicted with such disorders, can eliminate such swelling by a simple manipulation within a short time. In other words, the device 1 provides a very high therapeutic effect on swelling. In particular, its use in rehabilitation is highly effective.

In this example, prior to the application of the device 1, the above-mentioned patient's finger skin was swollen with a sense of fullness and was glossy with wrinkles disappeared. This made the fingers sausage-like resembling those of localized scleredema; the interphalangeal joints were all stuck in a bent position with both bending and stretching limited. Application of the present device 1 normalized the condition of the finger skin and also eliminated articular contracture.

Clinical Example 2

Figure 15:
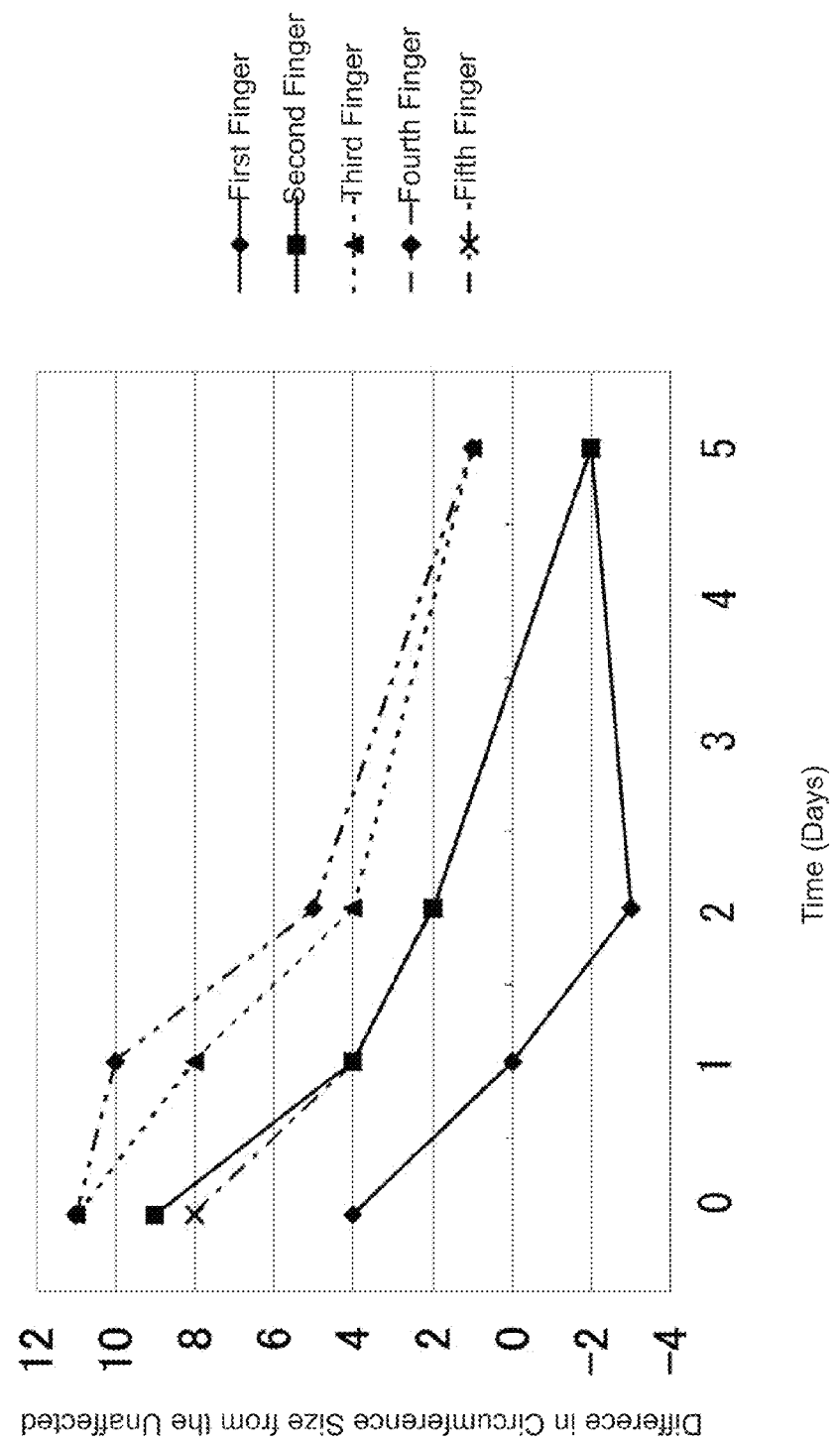
FIG. 15 is graph which shows a change in the finger circumference size (with the difference (mm) in the finger circumference size on the vertical axis and time (days) from the start of treatment on the horizontal axis.)

After a patient seen to have a swollen hand due to an extravasation form venous catheter has satisfactorily undergone an informed consent by the surgeon, the present device 1 was applied to said affected site (hand). The patient's condition prior to application of the device 1 was as follows. The patient being administered with Fesin for improving an anemic condition was subjected to an extravasation form venous catheter from the dorsum manus of the left hand toward the dorsal wrist side. This caused the hand to be diffusely swollen from the back of the hand to the fingers with observed considerable heat sensation, pain, and reddening along with limited finger bending as well. No improvement was seen with cooling and administration of analgesics. As active motion was started under compression using this device, the patient felt the pain alleviated. The motion of the fingers also substantially improved on the second day of the device 1 application. FIG. 15 shows the change in the difference between the circumference of the left hand and that of the right hand by the fifth day of the device 1 application. FIG. 15 shows that the circumference sizes of all left hand fingers from digitus primus (thumb) to digitus quintus (little finger) decreased, demonstrating that the left hand's swelling rapidly vanished. On the fifth day of the device 1 application, the swelling from the dorsal wrist to the fingers nearly vanished and it became possible to completely bend the fingers. In addition, applying the device 1 relieved the pain of the affected area. Thus application of the device 1 to the swelling from extravasation form venous catheter eliminates such swelling. Furthermore, the pain of the affected area was also relieved.

While many of the disorders included in work-related upper-extremities musculoskeletal disorders are caused by tenosynovial swelling, the above two clinical examples demonstrate that the present invention is capable of relieving not only hypodermic edema but also the edema developed in the deep tissues such as a synovial membrane and a ligament. This is because moving the hand makes it possible to compress the synovial membrane, thereby allowing the edema in an avascular deep tissue to be pushed out.

These characteristics make the present invention applicable not only to postoperative but also conservative treatment, in the work-related musculoskeletal disorders (including a carpal tunnel syndrome, stenosing tenosynovitis, and the like) generally called repetitive strain injury or cumulative trauma injury and the like. Its characteristics of relieving the edema of deep structures, such as a tendon and a ligament, is also a very attractive feature in the rehabilitation of a hand, which can be widely applied in this field. Further, for an application to the lower extremities, the devise can be expected to offer a preventive effect on deep venous thrombosis, which together with being disposable and highly portable, enables one to envision an application other than medical devices, such as a preventive measure against the economy class syndrome on plane, and the like. Thus, such a very extensive adaptation is anticipated.

Further, this positive pressure chamber for the extremities is applicable to the prevention and treatment of osteoarthritis affecting fingers mostly among females. Osteoarthritis afflicts at least 30% of those 60 years old and older, with the incidence rapidly increasing with age, but at the outset, light cases of swollen joints (arthritis, articular rheumatism) are noted in a substantial number of cases, in which the positive pressure chamber for extremities is capable of eliminating the swollen sites, thereby making it possible to prevent osteoarthritis. While osteoarthritis is recognized at least several dozen times as often as articular arthritis in patients, this device can relieve swelling or inflammation of the synovial membrane of a joint promptly through the promotion of lymphatic or venous perfusion; this action alleviates the arthritic symptoms seen in the articular rheumatism and osteoarthritis and inhibits the development thereof.

What is claimed is:

1. A positive pressure chamber for extremities comprising:
a bag-shaped member having a bag-shaped main part which is formed to inflate a space part defined by an exterior sheet member and an interior sheet member with fluid, said bag-shaped member being formed in such shape and size that, under a condition in which it is filled with fluid, it can cover the outer periphery of at least one of the extremities;
wherein said bag-shaped member is formed such that, when the space part is filled with the fluid, said extremity which is entirely covered with said interior sheet member is held under a positive pressure condition, and the distal end of said extremity can be moved in said space part, independently of other parts of the extremity; and
wherein said interior sheet member has an inlet, on the extremity's distal end side, for introducing the fluid that has been filled in the bag-shaped member and/or other fluid onto the outer periphery of the extremity and allows the fluid that is introduced therefrom to flow along a clearance between the outer periphery of the extremity and said interior sheet member in a direction away from the extremity's distal end; and said positive pressure chamber, further comprising:

a clearance securing member for securing said clearance for the fluid to flow between the outer periphery of said extremity and said interior sheet member.

2. The positive pressure chamber for extremities as set forth in claim 1, wherein:

said bag-shaped member is formed in such size and shape of securing a sufficiently sized space part that the interior sheet member which covers the extremity's distal end does not interfere with the exterior sheet member when the extremity's distal end is moved in the fluid filled in said space part.

3. The positive pressure chamber for extremities as set forth in claim 1, wherein said interior sheet member further has an extremity's distal end-accommodation part, which part is formed to cave in from said interior sheet member into said space part for accommodating at least one distal end of the extremities; and wherein:

said extremity's distal end accommodation part with the extremity's distal end inserted therein allows the extremity's distal end to move freely in the fluid filled in said space part.

4. The positive pressure chamber for extremities as set forth in claim 3, wherein said extremity's distal end accommodation part is shaped to fit the contour of the extremity's distal end.

5. The positive pressure chamber for extremities as set forth in claim 1, wherein said extremity is an arm including a hand, and said extremity's distal end is the hand and the fingers of the hand.

6. The positive pressure chamber for extremities as set forth in claim 1, wherein said extremity is a leg including a foot; and said extremity's distal end is the foot and toe.

7. The positive pressure chamber for extremities as set forth in claim 1, wherein the inlet formed in said interior sheet member allows said space part to communicate with the extremity's distal end, thereby introducing the fluid in said space part around the extremity's distal end.

8. The positive pressure chamber for extremities as set forth in claim 1, wherein the inlet formed in said interior sheet member is a large number of fine pores.

9. The positive pressure chamber for extremities as set forth in claim 1, wherein the inlet formed in said interior sheet member is a fluid-permeating sheet member provided at a site corresponding to the extremity's distal end.

10. The positive pressure chamber for extremities as set forth in claim 1, wherein the chamber has an outside-fluid inlet path for introducing a fluid other than the fluid in said space part around the extremity's distal end through said inlet of said interior sheet member.

11. The positive pressure chamber for extremities as set forth in claim 1, wherein said exterior sheet is provided with a fluid inlet port for introducing said fluid into the space part of said bag-shaped member.

12. The positive pressure chamber for extremities as set forth in claim 1, wherein said bag-shaped member is configured so as to cover the outer periphery of the extremity with said interior sheet member by folding it with said interior sheet member inside and the exterior sheet member outside, and wherein fasteners are provided at said edges of said exterior sheet member for joining, as folded, together the edges of the exterior sheet member themselves.

13. The positive pressure chamber for extremities as set forth in claim 1, wherein said interior sheet member is formed of a member which is more flexible than said exterior sheet member and is formed with sufficient anti-burst strength.

14. The positive pressure chamber for extremities as set forth in claim 1, wherein said exterior sheet member is formed of a transparent member to allow visually checking the movement of the extremity's distal end in the fluid filled therein.

15. The positive pressure chamber for extremities as set forth in claim 1, wherein the fluid filled in said space part is the atmosphere.

16. The positive pressure chamber for extremities as set forth in claim 1, wherein said other fluid is a draining fluid.

17. The positive pressure chamber for extremities as set forth in claim 1, wherein said draining fluid contains a drug to be administered into the body via the skin of said extremity.

18. The positive pressure chamber for extremities as set forth in claim 1, comprising:

a means for applying pulsation to the fluid introduced into the clearance between the outer periphery of the extremity and said interior sheet member.

19. The positive pressure chamber for extremities as set forth in claim 1, further comprising:

a flexible tube communicating with the space part of said bag-shaped member; and pump equipment for introducing fluid into said bag-shaped member through said tube, wherein:

the pressure of the fluid filled in said bag-shaped member by said pump equipment is a positive pressure sufficient to hold said extremity within said fluid, and is at a value within the range of equilibrium state with a normal interstitial pressure of said extremity.

20. The positive pressure chamber for extremities as set forth in claim 19, wherein:

the pressure value of the fluid filled in said bag-shaped member by said pump equipment is not less than 20 mmHg but less than the diastolic blood pressure.

21. The positive pressure chamber for extremities as set forth in claim 19, comprising:

a means to maintain the pressure of the fluid filled in said bag-shaped member by said pump equipment constant throughout the time that said positive pressure chamber for extremities is operated.

22. The positive pressure chamber for extremities as set forth in claim 1, further comprising:

a pressure control valve for maintaining the pressure within the space part of said bag-shaped member at a designated value.

23. The positive pressure chamber for extremities as set forth in claim 1, further comprising:

a means for controlling the temperature, moisture, or both, of the fluid filled in the space part of said bag-shaped member and/or a fluid which is introduced from said inlet into the clearance between the outer periphery of the extremity and said interior sheet member.

24. The positive pressure chamber for extremities as set forth in claim 1, wherein:
said clearance-securing member is worn beforehand on said extremity before the extremity is applied to said bag-shaped member.

25. The positive pressure chamber for extremities as set forth in claim 1, wherein:
said clearance-securing member is fixed to a part of said interior sheet member which comes in contact with the outer periphery of said extremity.

26. The positive pressure chamber for extremities as set forth in claim 1, further comprising:
a fluid recovery means for recovering the fluid which has flowed along the clearance between the outer periphery of the extremity and said interior sheet member in a direction away from the extremity's distal end.

27. The positive pressure chamber for extremities as set forth in claim 1 is for controlling edema and pain after extremity surgery.

28. The positive pressure chamber for extremities as set forth in claim 1 is for providing post-surgical management for work-related musculoskeletal disorders.

29. The positive pressure chamber for extremities as set forth in claim 1 is for providing conservative treatment for work-related musculoskeletal disorders.

30. The positive pressure chamber for extremities as set forth in claim 1 is for use in a transdermal drug delivery.

31. The positive pressure chamber for extremities as set forth in claim 1, wherein said clearance securing member has a stocking-shape.

* * * * *